(12) United States Patent
Schramm et al.

(10) Patent No.: US 8,666,494 B2
(45) Date of Patent: Mar. 4, 2014

(54) HEADER FOR IMPLANTABLE PULSE GENERATOR AND METHOD OF MAKING SAME

(75) Inventors: Dana E. Schramm, Woodbury, MN (US); Matthew L. Iwen, Savage, MN (US); Nick J. Miller, Blaine, MN (US); Matthew R. Call, Blaine, MN (US)

(73) Assignee: Donatelle Plastics, Inc., New Brighton, MN (US)

( * ) Notice: Subject to any disclaimer, the term of this patent is extended or adjusted under 35 U.S.C. 154(b) by 245 days.

(21) Appl. No.: 13/093,455

(22) Filed: Apr. 25, 2011

(65) Prior Publication Data

US 2011/0270363 A1 Nov. 3, 2011

Related U.S. Application Data

(60) Provisional application No. 61/329,173, filed on Apr. 29, 2010.

(51) Int. Cl.
*A61N 1/02* (2006.01)

(52) U.S. Cl.
USPC .......................................................... 607/37

(58) Field of Classification Search
USPC .......................................................... 607/37
See application file for complete search history.

(56) References Cited

U.S. PATENT DOCUMENTS

| | | |
|---|---|---|
| 3,811,045 A | 5/1974 | Turner et al. |
| 4,167,379 A | 9/1979 | Liautaud |
| 4,383,964 A | 5/1983 | Prus |
| 4,441,498 A | 4/1984 | Nordling |
| 4,469,104 A | 9/1984 | Peers-Trevarton |
| 4,471,787 A | 9/1984 | Bentall |
| 4,684,202 A | 8/1987 | House et al. |
| 4,772,761 A | 9/1988 | Ibrahim et al. |
| 4,855,868 A | 8/1989 | Harding |
| 4,898,173 A | 2/1990 | Daglow et al. |
| 4,934,366 A | 6/1990 | Truex et al. |
| 5,076,270 A | 12/1991 | Stutz, Jr. |
| 5,261,395 A | 11/1993 | Oleen et al. |
| 5,304,219 A | 4/1994 | Chernoff et al. |
| 5,326,272 A | 7/1994 | Harhen et al. |
| 5,375,183 A | 12/1994 | Edwards et al. |
| 5,453,029 A | 9/1995 | Moldenhauer et al. |
| 5,456,698 A | 10/1995 | Byland et al. |
| 5,470,238 A | 11/1995 | Walden |
| 5,662,692 A | 9/1997 | Paspa |
| 5,843,141 A | 12/1998 | Bischoff et al. |
| 6,111,554 A | 8/2000 | Chufarovsky et al. |
| 6,113,583 A | 9/2000 | Fowles |
| 6,183,305 B1 | 2/2001 | Doan et al. |
| 6,331,737 B1 | 12/2001 | Lim et al. |
| 6,441,741 B1 | 8/2002 | Yoakum |

(Continued)

FOREIGN PATENT DOCUMENTS

WO    WO 2009/126872    10/2009

*Primary Examiner* — Carl H Layno
*Assistant Examiner* — Jon Eric C Morales
(74) *Attorney, Agent, or Firm* — Thomas J. Nikolai; Nikolai & Mersereau, P.A.

(57) ABSTRACT

A header for use in implantable pulse generator devices. The header is part of electrical connector assembly having one or more openings designed to receive the terminal pin of an electrical lead wire or electrode. The header is designed to provide and sustain long-term electrical and mechanical lead wire connections between the electrodes of a terminal pin and the implantable pulse generator device.

17 Claims, 5 Drawing Sheets

(56) References Cited

U.S. PATENT DOCUMENTS

| | | |
|---|---|---|
| 6,544,816 B1 | 4/2003 | Lim et al. |
| 6,778,089 B2 | 8/2004 | Yoakum |
| 6,817,905 B2 | 11/2004 | Zart et al. |
| 6,912,423 B2 | 6/2005 | Ley et al. |
| 7,083,474 B1 | 8/2006 | Fleck et al. |
| 7,133,722 B2 | 11/2006 | Hansen et al. |
| 7,175,482 B2 | 2/2007 | Zart et al. |
| 7,299,095 B1 | 11/2007 | Barlow et al. |
| 7,309,262 B2 | 12/2007 | Zart et al. |
| 7,472,505 B2 | 1/2009 | Zart et al. |
| 7,601,033 B2 | 10/2009 | Ries et al. |
| 7,654,843 B2 | 2/2010 | Olson et al. |
| 7,682,202 B2 | 3/2010 | Arnholt et al. |
| 7,717,754 B2 | 5/2010 | Ries et al. |
| 2003/0069612 A1 | 4/2003 | Zart et al. |
| 2003/0163171 A1 | 8/2003 | Kast et al. |
| 2004/0167582 A1 | 8/2004 | Tvaska et al. |
| 2005/0186829 A1 | 8/2005 | Balsells |
| 2006/0264122 A1 | 11/2006 | Aman et al. |
| 2008/0255631 A1* | 10/2008 | Sjostedt et al. .............. 607/37 |

\* cited by examiner

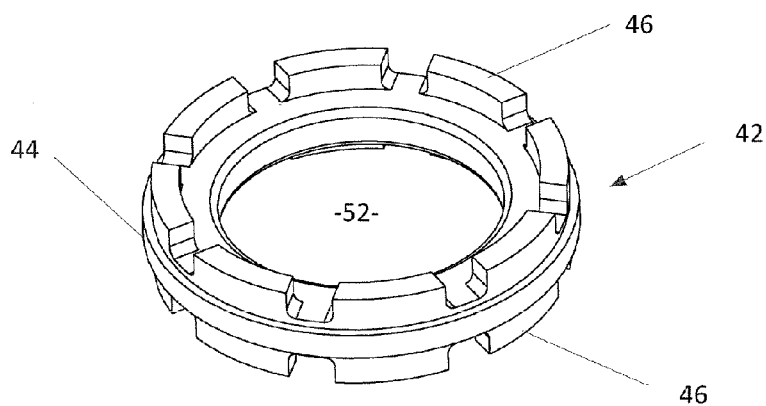
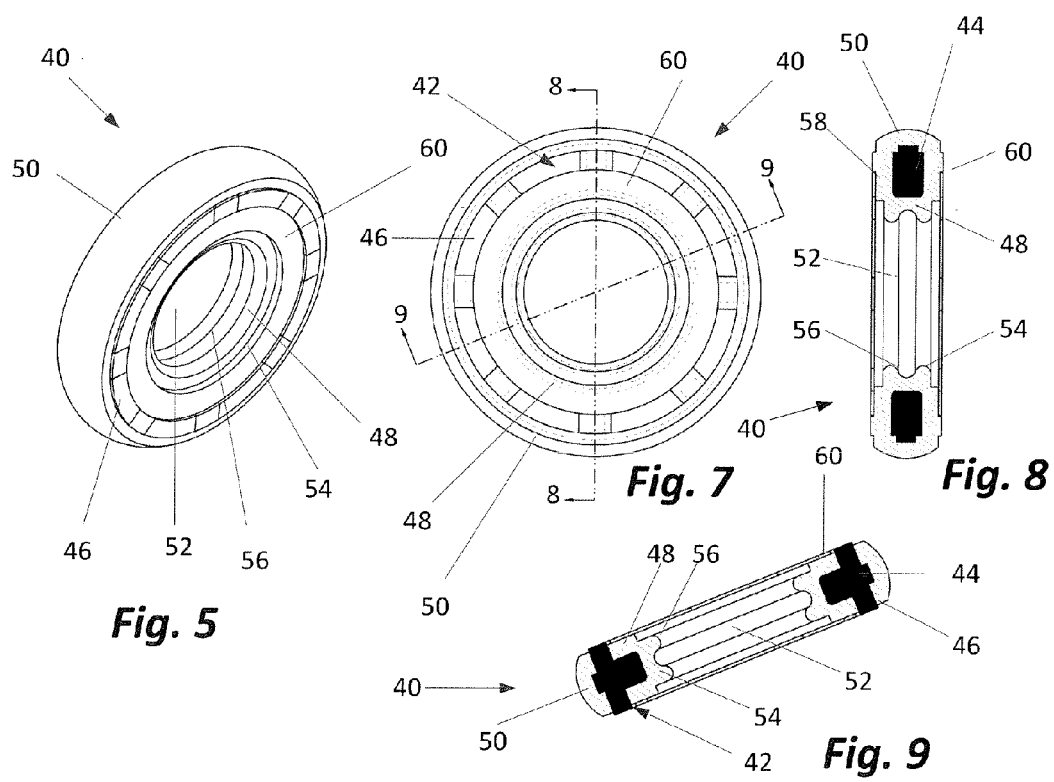
*Fig. 6*
*Fig. 5*
*Fig. 7*
*Fig. 8*
*Fig. 9*

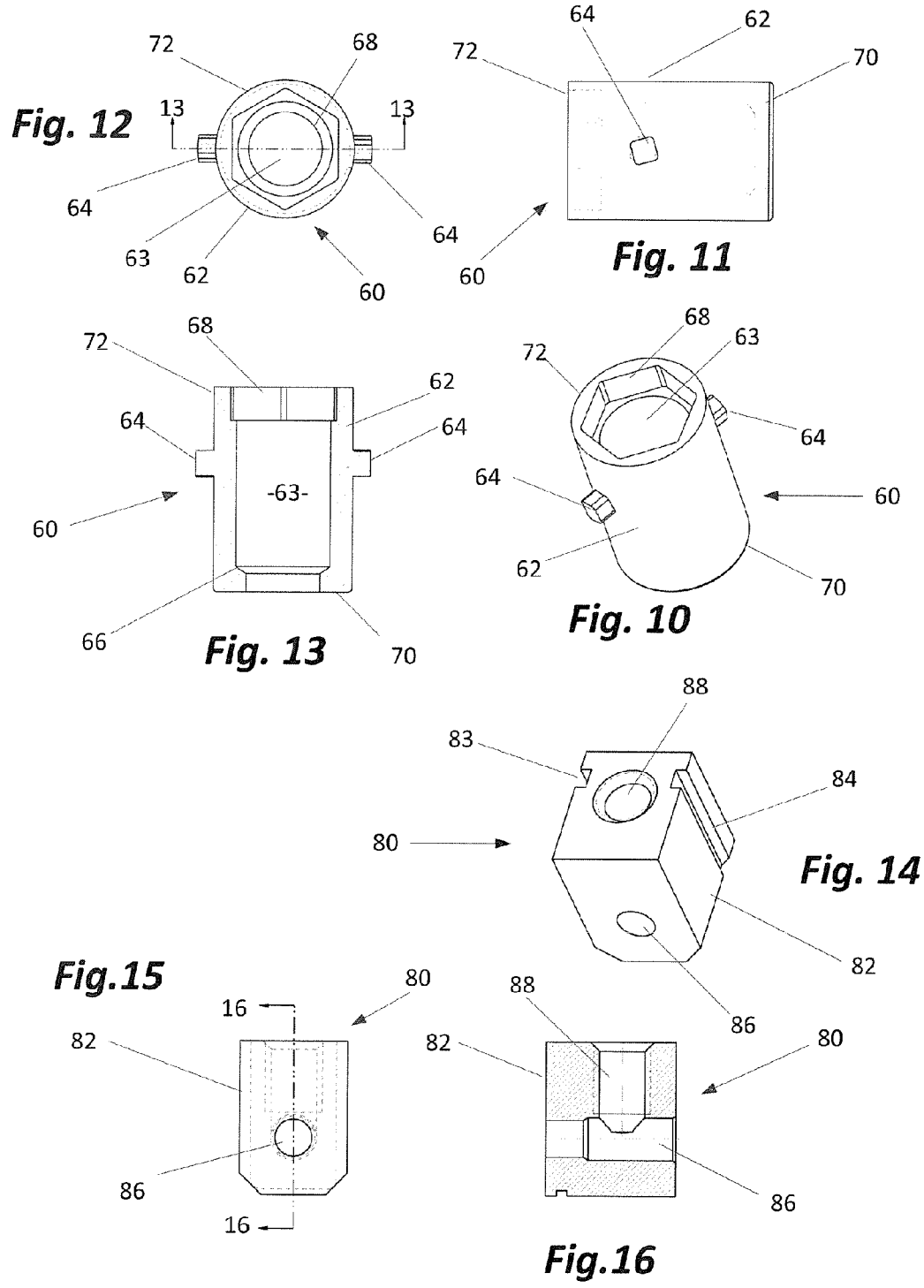

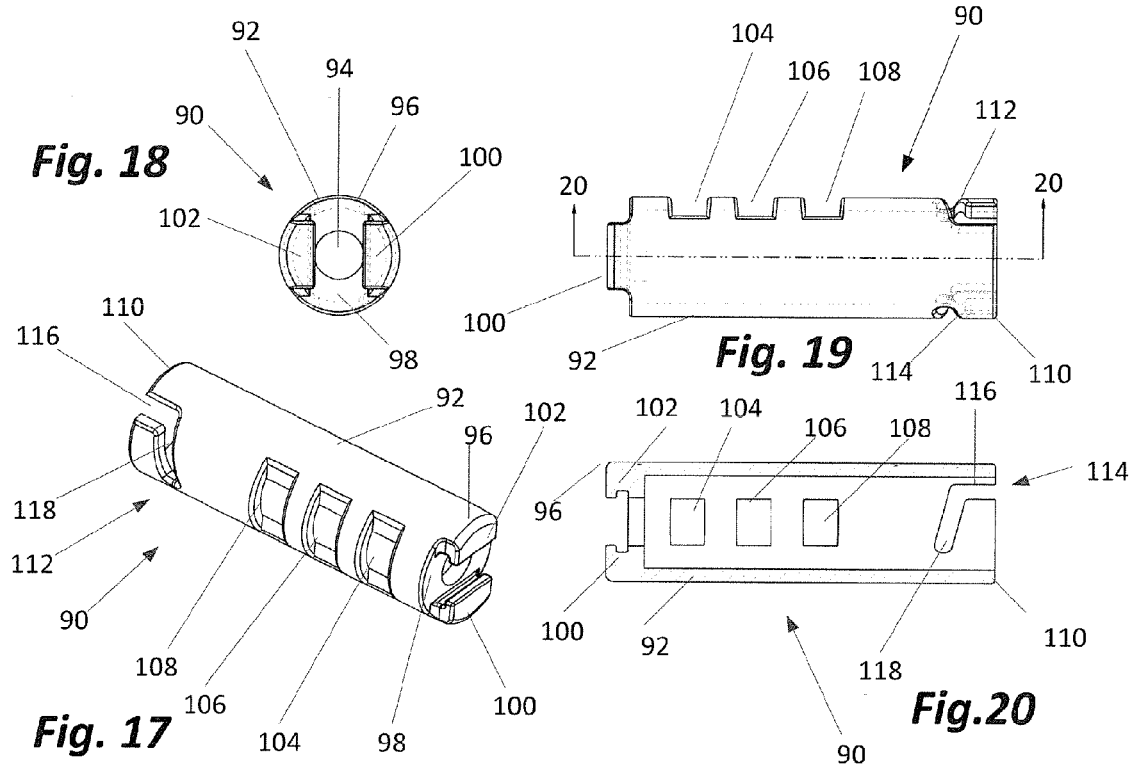
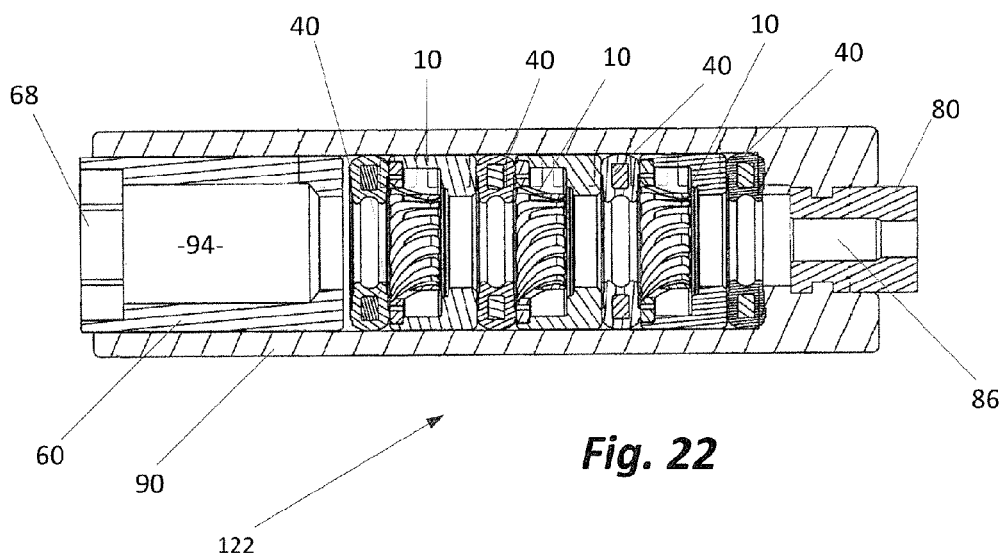

HEADER FOR IMPLANTABLE PULSE GENERATOR AND METHOD OF MAKING SAME

CROSS-REFERENCED TO RELATED APPLICATIONS

This application is a non-provisional application of application Ser. No. 61/329,173, filed Apr. 29, 2010 and claims priority from that application which is also deemed incorporated by reference in its entirety in this application.

STATEMENT REGARDING FEDERALLY SPONSORED RESEARCH OR DEVELOPMENT

Not applicable.

BACKGROUND OF THE INVENTION

I. Field of the Invention

The present invention, relates to implantable pulse generators and, more particularly, implantable pulse generator headers and components of such headers. The present invention also relates to methods for manufacturing headers for implantable pulse generators.

II. Discussion of Related Art

In medical technology an implanted pulse generator (IPG) may be employed for a variety of purposes. An IPG is a battery powered device designed to deliver electrical stimulation to the body. An IPG is typically an integral component of a surgically implanted system, which includes the IPG, one or more leads and an external programmer. Such systems are used, for example, to provide deep brain stimulation, vagus nerve stimulation, heart defibrillation, management of heart rhythms, or treatment of other disorders.

The IPG is typically implanted within a person's body, usually beneath the clavicle. Leads are then routed through the body between the site to be stimulated and the IPG. The leads are then coupled to the header of the IPG to carry signals between the IPG and the treatment site. The IPG can be calibrated using the external programmer by a physician (such as an electrophysiologist, neurologist or cardiologist) or by a nurse or other trained technician to meet the individual patient's needs. The IPG must be replaced periodically upon battery depletion. Battery depletion can occur within three to five years, though battery life is dependent on individual usage. End of battery life can be reasonably predicted by the use of a telemetry between the IPG and the external programming device. This allows the IPG to be replaced prior to battery failure.

One example of an IPG is a heart pacemaker (or artificial heart pacemaker, so as not to be confused with the heart's natural pacemaker), a medical device which uses electrical impulses to regulate the beating of the heart. When the IPG is employed as an artificial heart pacemaker, the IPG is used in combination with a lead comprising a set of electrodes which carry stimulation pulses from the IPG to the heart and electrical signals back from the heart to the IPG which senses and responds to such signals. The primary purpose of a pacemaker is to maintain an adequate heart rate, either because the heart's native pacemaker is not fast enough, or because there is a block in the heart's electrical conduction system. Modern pacemakers are externally programmable and allow the electrophysiologist to select the optimum pacing modes for individual patients. Some IPG devices combine a pacemaker and defibrillator in a single implantable device. Multiple electrodes stimulating differing positions within the heart are often used to improve synchronization of the contractions of the upper and lower and chambers of the heart.

Another type of IPG is an implantable cardioverter-defibrillator (ICD), a small battery-powered electrical pulse generator which is implanted in patients who are at risk of sudden death due to ventricular fibrillation or ventricular tachycardia. The device is programmed to detect cardiac arrhythmia and correct it by delivering a jolt of electricity. In current variants, ICD devices have the ability to treat both atrial and ventricular arrhythmias as well as the ability to perform biventricular pacing in patients with congestive heart failure or bradycardia.

The process of implantation of an ICD is similar to implantation of a pacemaker. Like pacemakers, ICD devices are coupled to a set of leads containing electrode (s) and wire (s) which are passed though the vasculature to desired locations in the heart. For example an electrode can be passed through a vein to the right chambers of the heart, and then lodged in the apex of the right ventricle. Providing defibrillation pulses at this location has been found to be advantageous. As is the case with pacemaker leads, the leads are coupled to the header of the ICD and used to carry both stimulation pulses from the ICD to the heart and electrical signals from the heart to the ICD.

ICDs constantly monitor the rate and rhythm of the heart and can deliver therapies, by way of an electrical shock, when the electrical manifestations of the heart activity exceed one or more preset thresholds. More modern devices can distinguish between ventricular fibrillation and ventricular tachycardia (VT) and may try to pace the heart faster than its intrinsic rate in the case of VT, to try to break the tachycardia before it progresses to ventricular fibrillation. This is known as fast-pacing, overdrive pacing or anti-tachycardia pacing (ATP). ATP is only effective if the underlying rhythm is ventricular tachycardia, and is never effective if the rhythm is ventricular fibrillation.

Other IPG devices served as neurostimulators used to treat pain, incontinence, and other neurologic and muscular conditions. Such IPG devices have a header used to couple the IPG to leads containing a plurality of wires and electrodes which deliver stimulating pulses from the IPG to nerves and muscles to provide beneficial therapies. The electrodes and wires of the leads may also be used to carry electrical signals back to the IPG.

The various types of IPG devices referenced above typically have a header to which the leads are attached. The header typically includes one or more bores each configured to receive a terminal pin of a lead. The terminal pin will typically contain a plurality of electrodes spaced along its length. Likewise, the bore will typically have a matching set of electrical contacts along its length which are spaced to form electrical connections with the electrodes of the lead pin. The electrical connections should be isolated from each other to prevent a short or unintended propagation, of signals along a particular channel. The number and spacing or the electrodes and contacts may vary, but standards have emerged related to such numbers and such spacing for various types of stimulation systems.

Previous header designs and manufacturing techniques have resulted in difficulty in maintaining component alignment, spacing, and isolation. Likewise, previous header designs and manufacturing techniques made it difficult, if not impossible, to adequately test the assembly before it was fully complete. If testing demonstrates an issue exists with the header after manufacturing is complete, the entire header needs to be discarded and typically none of the components can be salvaged. Thus, to date there has been a real need in the art for a custom solution allowing for interim testing of the electrical, components of a bore of a header and the assembly thereof before overmolding of the components is performed to complete the manufacture of the header. More specifically, there is a real need for product design and manufacturing methods which allow conformance to be assessed prior to final part, generation, increasing assurance the product meets performance requirements while at the same time decreasing the risk, of needing to scrap a more expensive finished product.

The inventors also believe previous devices and manufacturing methods create difficulty in maintaining the desired balance between mechanical and electrical properties. Examples of deficiencies include: (1) a strong mechanical insertion force resulting in excessive pressure exerted on the inner seal and electrical components of the bore; (2) excessive electrical contact resulting in shorts or faults which can draw off potential battery power; (3) insufficient retention forces resulting in an electrode of the bore losing position or falling out of place; and (4) manufacturing tolerances which create challenges related to meeting the electrical and mechanical conformance requirements. The tolerances of the electrode lead wires present further challenges with respect to the header's ability to achieve the desired electrical and mechanical responses. There exists a real and substantial need to provide efficient and cost effective manufacturing methods and designs which meet these challenges.

Prior art header designs often comprise various thin wire connections. Notable are those composed a of spring-type connector in the form of a female leaf spring, canted coil spring or wire "slide by" connector. The inventors believe these devices offer an adequate electrical connection, but are fragile in design. Such connectors can be damaged or broken easily upon insertion of lead pins into the bore. In addition, current designs are expensive to manufacture requiring multiple component pieces and challenging assembly steps driving up cost.

Prior art header designs also provide seals which are intended to isolate the electrical channels, but are subject to failure either during manufacture or as a result of the insertion or removal of lead pins. These seals can also result in alignment problems which arise during overmolding, typically one of the last steps in the manufacturing process. If during overmolding the molding pressures or temperatures deform the seals in an unintended manner, improper alignment of the components and improper sealing can occur. To avoid such problems, thermoset rather than thermoplastic materials requiring lower molding pressure, but longer molding cycle times have often been employed. While the resulting header will work, the header is expensive and time consuming to manufacture. Also, whatever materials and molding techniques are used, great care must be taken to ensure proper alignment and isolation increasing the level of skill and care required to manufacture the header.

For the reasons set forth above, assembly of IPG devices is currently very labor-intensive and time-consuming, and requires skilled craftsmanship on the part of each person performing the assembly steps. In prior assembly methods, each individual component of the bore of the header is individually placed and aligned, either by press fitting and/or fixturing, in a cavity block which is either pre-molded or yet to be cast. Problems associated with these techniques include: electrical leakage between components, electrical failures and excessive force required for inserting and withdrawing lead pins. Such manufacturing techniques result in a high scrap rate and a high scrap cost, since failures are detected only after completion of whole device assembly. Furthermore the final assembly is confined to a specific outer casting design.

SUMMARY OF THE INVENTION

Numerous advantages are obtained when manufacturing a header for an implantable pulse generator by:
  a. Forming a plurality of spring contact rings, each spring contact ring having a bore; a plurality of ring seals, each ring seal having a bore; a sleeve having a wall surrounding a bore; and a strain relief having a bore;
  b. Forming a subassembly by (a) inserting at least some of the plurality of spring contact rings and at least some of the plurality of ring seals into the bore of the sleeve such that each spring contact ring is separated from any adjacent spring contact ring by a ring seal, and (b) inserting at least a portion of the strain relief into the bore of the sleeve to secure the spring contact rings and ring seals in a position in which adjacent spring contact rings and ring seals are in contact with each other and the bores through the strain relief and each of the spring contact rings and rings seals of the subassembly are aligned with each other;
  c. Inserting a molding pin through the bores of the strain relief and each of the spring contact rings and ring seals of the subassembly;
  d. Overmolding the subassembly to lock the spring contact rings, ring seals and strain relief of the subassembly in position; and
  e. Removing the molding pin.

The method manufacture outlined above makes it possible to test the subassembly before performing the overmolding step. Also, the step of overmolding may be performed at a pressure or annealing temperature which partially collapses the wall of the sleeve to lock the spring contact rings, ring seals and strain relief of the subassembly in position with respect to each other and electrically isolate each of the spring contact rings of the subassembly from each other through the cooperation of the wall of the sleeve and the ring seals of the subassembly.

Further, the sleeve can be constructed so as to include a plurality of windows such that there is a window adjacent to each of the spring contact rings of the subassembly. A wire can be passed through a window and electrically coupling to the spring contact ring adjacent to the window to form an electrically conductive path through the sleeve. During the overmolding step, some of the material used to perform the overmolding step enters the windows to assist in locking at least, one of the spring contact rings in position. The wire can be installed either before or after the overmolding step. If the wire is installed after the overmolding step, it may be advantageous to prevent the overmold material from occluding the window.

Likewise, either the strain relief or the sleeve can include a projection with the other of the stain, relief or sleeve including a channel. The channel should have a straight section and a camming section angled from the straight section. The strain relief can thereby be temporarily locked to the sleeve by moving the strain relief into the bore of the sleeve until the projection reaches the camming section, and then twisting the strain relief relative to the sleeve to cause the projection to enter the camming section. So that the same sleeve can be used with different combinations of spring contact rings and ring seals, the camming section may angled from the straight section at an angle other than 90 degrees. Thus, when the sleeve and strain relief are rotated relative to each other, the strain relief is drawn tight against the collection of spring contact rings and ring seals within the sleeve. During the overmolding step, some of the material used to perform the overmolding step enters the channel to assist in locking at least the strain relief in position.

Problems encountered in the prior art can also be alleviated by providing unique and novel ring seals. The ring seals may be constructed to include a deformable outer wall, a deformable inner wall defining a bore through the ring seal, a pair of side walls and a rigid core having exposed portions along each of the sidewalls. The exposed portions of the rigid core act as stops for maintaining a predefined minimum distance between two of the adjacent spring contact rings. Providing such a core offers additional advantages in that the rigid core also prevents the inner diameter of the ring seal from deforming during the overmolding step even as the outer diameter of the sealing ring deforms. The inner core may, for example, be made of PEEK and the other portions of the ring seal of silicone.

Various problems are also resolved by providing unique and novel spring contact rings which include a ring and a spring having spiral, radial cut spring fingers. This arrangement provides a spring with a longer beam deflection than those typically used while retaining a compact overall shape. Such a spring also ensures good contact between the spring and an electrode of a lead pin. The design allows the spring to be more robust reducing the risk that the spring will break during normal use, and particularly during insertion or retraction of a lead pin. During the overmolding step, the molding pin engages a molding pin. The spring contact ring adequately resists molding pressures typically encountered.

The sleeve may be made of any suitable material. Examples include, but are not limited to PEEK, polyurethane and polysulfone. The thickness of the wall of the sleeve will depend on the material from which the sleeve is constructed and the molding pressure used during overmolding. The material and molding pressure should be selected to permit the sleeve to deform to firmly lock the components of the subassembly in place. The sleeve may also be designed to include structures on its outer surface for supporting at least one other component of the header. Such other component could be an RE antenna, another subassembly, or any other desired component to be included in the header.

DESCRIPTION OF DRAWINGS

FIG. 5 is a perspective view of a ring seal;
FIG. 6 is a perspective view of the core of the ring seal of FIG. 5;
FIG. 7 is an end view of the ring seal of FIG. 5;
FIG. 8 is a cross-sectional view of the ring seal taken through line 8-8 of FIG. 7;
FIG. 9 is a cross-sectional view of the ring seal taken through line 9-9 in FIG. 7;
FIG. 10 is a perspective view of a strain relief;
FIG. 11 is a side view of the strain relief of FIG. 10;
FIG. 12 is an end view of the strain relief of FIG. 10;
FIG. 13 is a cross-section of the strain relief through line 13-13 of FIG. 12;
FIG. 14 is a perspective view of a tip block;
FIG. 15 is a bottom view of the tip block of FIG. 14;
FIG. 16 is a cross-sectional view of the tip block through line 16-16 of FIG. 15;
FIG. 17 is a perspective view of a sleeve;
FIG. 18 is an end view of the sleeve of FIG. 17;
FIG. 19 is a side view of the sleeve of FIG. 17;
FIG. 20 is a cross-sectional view of the sleeve through line 20-20 in FIG. 19;
FIG. 22 is a cross-sectional view of the sleeve of FIG. 17 showing a subassembly comprising various components coupled to the sleeve.

DESCRIPTION OF PREFERRED EMBODIMENT

Figure 1:
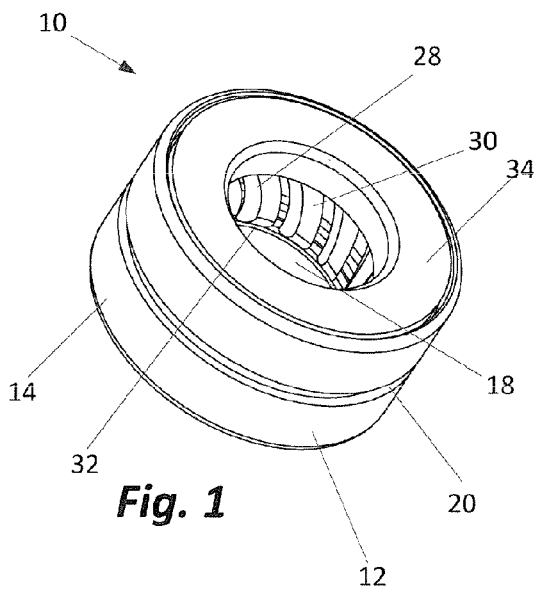
FIG. 1 is a perspective view showing a spring contact ring.
Figure 2:
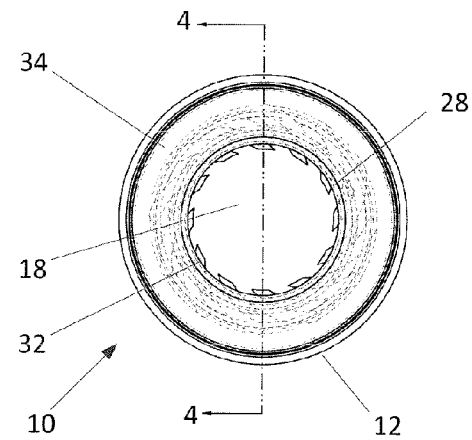
FIG. 2 is an end view of the spring contact ring of FIG. 1.

The following discussion is presented to enable a person skilled in the art to make and use the present teachings. Various modifications to the illustrated embodiments will be readily apparent to those skilled in the art, and the principles described herein may be applied to other embodiments and applications without departing from the present invention. Thus, the present invention is not intended to be limited to embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended, to limit the scope of the present invention. Skilled artisans will recognize many useful alternatives to the teachings and the examples provided herein falling within the scope of the invention exist and may be employed without deviating from the invention.

Embodiments of the present invention include electrical contacts. Various types of electrical contacts may be used. By way of example, such electrical contacts may be in the form of a spring contact ring composed of flanged internal fingers shaped and cut in a matter to sustain long term electrical, and mechanical lead wire connections when used in implantable pulse generator (IPG) devices. The spring contact ring is designed to sustain contact between the pulse generator and an electrode (lead wire) of a lead pin through which electrical impulses are transmitted to or from the body tissue. The spring contact ring maintains mechanical force and alignment requirements with an electrode of a lead pin when the lead pin is inserted and retained to the pulse generator header in order to sustain, the desired electrical connection. The spring contact ring should not be susceptible to damage by insertion or removal of the lead pin.

Typically, a header made in accordance with the present invention, will have a number of electrical connectors aligned in a row which separately engage electrodes on the lead pin. It is therefore important to physically and electrically isolate the electrical connectors from each other to prevent current leakage or propagation of signals along unintended electrical paths. Therefore, the electrical connectors should be separated by a seal member. Maintaining proper spacing and alignment between the electrical connectors is also important since each electrical connector of the lead is intended to be coupled to a separate electrode of the lead pin. More specifically, the spacing of the electrical connectors of the header must correspond to the spacing of the electrodes of the lead pin.

Embodiments of the present invention also include a sleeve designed to contain various connector and seal components. This assembly is unique in the way it incorporates a sleeve to maintain component alignment throughout the manufacturing process. This can allow for a less expensive method of manufacturing requiring less assembly time (labor) and less material usage. In addition the component sleeve can be multi-functional, as it can be employed in various overmolded header designs, without the setup and redesigns required by existing methods. The manufacturing method is module based. Elements of the manufacturing method typically include: (1) manufacturing individual components, e.g., connectors, seals, and sleeves; (2) creating a subassembly from such components, electrical connectors and seals; (3) testing the subassembly to ensure conformance to manufacturing standards; and (4) over molding the subassembly.

Embodiments of the present invention disclose a sleeve which cooperates with various components to keep the components in alignment. The inventors have found it more efficient to manufacture using the sleeve in combination with other components to create a subassembly which can be tested prior to overmolding.

FIGS. 1-4 show a spring contact ring 10 of a type which may be employed when practicing the present invention. The spring contact ring 10 includes an outer housing 12. The outer housing 12 comprises an outer wall 14 and an inner wall 16 surrounding an aperture or bore 18. The outer wall 14 includes a recessed channel 20. The inner wall 16 includes a flange 22 and a stop surface 23.

Figure 3:
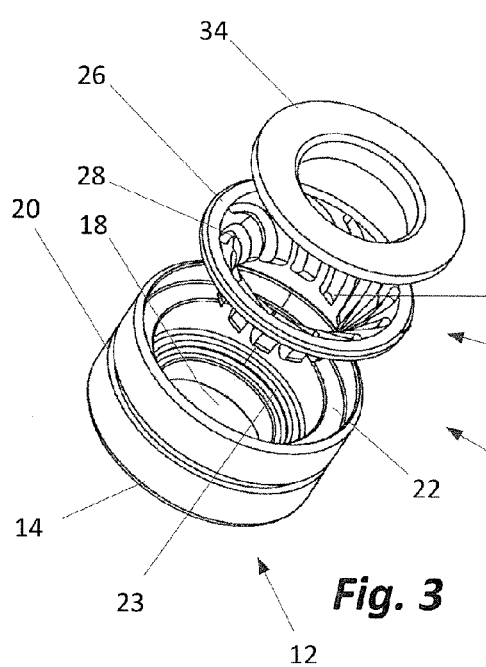
FIG. 3 is an exploded view showing the components of the spring contact ring of FIG. 1.
Figure 4:
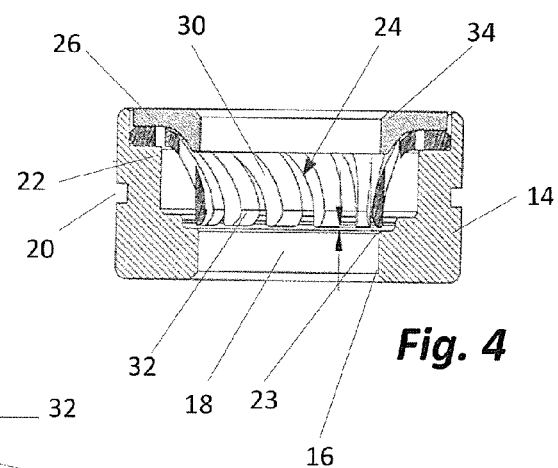
FIG. 4 is a cross-sectional view of the spring contact ring of FIG. 1.

The spring contact ring 10 also includes a spring 24. Spring 24 includes a base 26. Extending from the base 26 is a plurality of spring fingers 28. Each spring finger 28 includes a flange portion 30 terminating in an electrical contact zone 32. As best shown in FIGS. 3 and 4, the fingers 28 are all cut or otherwise formed in a radial fashion to provide a longer beam deflection and, at the same time, a compact overall shape.

When the spring contact ring 10 is assembled, the base 26 of the spring 24 engages the flange 22 and is either directly welded to the flange 22 or sandwiched between the flange 22 and a cap 34 which is secured to the inner wall 16 of the housing 12 to secure the spring 24 in place. Neither the flange portion 30 nor the electrical contact zone 32 of fingers 23 are permanently secured to any structure other than the base 26 of the spring 24 and the fingers 28 are permitted to flex within the bore 18. When either a molding pin (not shown) or a lead pin (not shown) is inserted through bore 18 of the spring contact ring 10, the outward movement of the fingers 28 is constrained by the stop surface 23 of the inner wall 16 of the outer housing 12. The fingers 28 may be biased toward the longitudinal axis of the bore 18. In one alternative arrangement, the electrical contact zone 32 of each finger 28 is pinched between a lead pin (or molding pin) and the stop surface 23 when such a pin is inserted through the bore 18 to provide sold physical contact between the pin and the electrical contact zone 32. In another alternative arrangement, the pin contacts the inner wall of the housing adjacent the stop surface, but does not cause the spring fingers to contact the stop surface. This is beneficial during overmolding because the mold pin supports the ring sufficiently to resist molding pressure without the risk of damaging the spring fingers. In any case, the stop surface prevents over-bending of the spring fingers 28 during insertion of a lead pin or molding pin.

Electrical connector ring 10 in inexpensive to make by requiring less manufacturing steps as the process uses more adaptable CNC machining or metal injection molding (MIM) methods requiring less setup, fewer parts and minimal assembly, lowing associated manufacturing costs. Materials of construction which may be used to make spring contact ring 10 include, but are not limited to, alloys of stainless steel 316L, titanium, MP35N, or nitinol.

Spring contact rings, such as spring contact ring 10, provide a stronger structure than the coil or wire springs which may also be employed. As such, spring contact ring 10 is less likely to break or crack.

FIGS. 5-9 illustrate a ring seal 40 having an advantageous construction. The ring seal 40 has a core 42. The core 42 includes a ring-shaped base structure 44. Extending outwardly from the base structure 44 is a plurality of stops 46. The core 42 is preferably made of a first material which is stiff, durable and a non-conductive plastic such as PEEK. The core 42 is overmolded with a second material which is softer and resilient such as silicone rubber. As shown, the ring seal 40 has an inner portion 48 and an outer portion 50 each made of the second material. The inner portion 48 surrounds an aperture or bore 52 and has a pair of sealing lobes 54 and 56 extending into the bore 52. The ring seal 40 also has a first side wall 58 and a second side wall 60. The side walls 58 and 60 are also made of the second material, but the ends of the stops 46 are left exposed when the core 42 is overmolded with the second material.

The ring seal 40 offers a number of advantages. The stops 46 can be used to register and maintain proper spacing between adjacent components. The lobes 54 and 56 engage a lead pin (or molding pin) inserted into the bore 52 to form a suitable seal. The core generally inhibits compressive forces which may deform on the outer portion 50 from being transferred to and deforming to an unacceptable degree the inner portion 43. Likewise, the core inhibits forces causing deformation of the inner portion 48 from deforming the outer portion 50 to any unacceptable degree.

FIGS. 10-13 show a strain relief. The strain relief 60 comprises a cylindrical wall 62 surrounding a central passage or bore 63. Extending outwardly from the cylindrical wall 62 is a pair of locking projections 64. The central passage is shown as including shoulder 66 at one end and a hexagonal interior surface 68 at the other. Alternative shapes may be used in lieu of a hexagonal shape without deviating from the invention. The two ends 70 and 72 are open to the central passage or bore 63.

FIGS. 14-16 show a set screw block 80. The set screw block 80 (also referred to as a tip block) has an outer wall 82 with a pair of alignment, channels 83 and 84. The interior of the set screw block 80 includes a pin-receiving channel or bore 86 extending through the block 80 in a direction generally perpendicular to the alignment channels 83 and 84. The set screw block 80 also includes a threaded set screw channel 88 which extends generally perpendicularly from channel 86 and receives a set screw (not shown) which is used to lock in place a pin (not shown) inserted into the pin-receiving channel. While a set screw block 80 has been shown and described, other locking mechanism arrangements are known which may alternatively be employed to lock the pin in place.

FIGS. 17-20 show an electrical connector sleeve 90. The electrical connector sleeve 90 comprises a generally cylindrical outer wall 92 surrounding a central bore 94. One end 96 of the sleeve 90 includes a shoulder 98 and a pair of fingers 100 and 102. Spaced along the length of the cylindrical outer wall 92 is a plurality of windows. Three such windows 104, 106 and 108 are shown. These windows extend through the outer wall 92.

Extending inwardly from end 110 of the outer wail 92 is a pair of strain relief locking channels 112 and 114. The strain relief locking channels 112 and 114 each include a straight section 11.6 extending inwardly from end 110 and a camming section 118 projecting at an angle from the straight section 116. As best shown in FIG. 20, this angle can be greater than 90° for reasons explained below.

To provide an electrical path between each individual spring contact ring 10 eventually located within the sleeve and the exterior of the sleeve 90, one end of an electrical conductor (not shown) may be passed through one of the windows 104, 106 or 108 adjacent to the spring contact ring 10 and coupled to the spring contact ring 10. The recess channel 20 of the spring contact ring 10 may be employed, to create a coupling between the end of the electrical conductor and the spring contact ring 10.

Sleeve 90 can be composed of various rigid materials, encompassing: (1) either amorphous or semi-crystalline polymers within the categories defined as engineering, high performance or ultra polymers, including poly-ethyl-ethyl-ketone, polysulfone, polyurethane, polyphenylene, polyimides, liquid crystal, polycarbonate, polyamide, ABS, COC, or alloys thereof; (2) ceramics, or; (3) metallic materials such as of Si 316L, MP35N and titanium. Certain advantages are achieved by forming the sleeve 90 of a material such as PEEK, polyurethane or polysulfone of a suitable thickness which will allow the sleeve to compress when exposed to overmolding pressures or annealing temperatures to lock components within the sleeve 90 in place.

Figure 21:
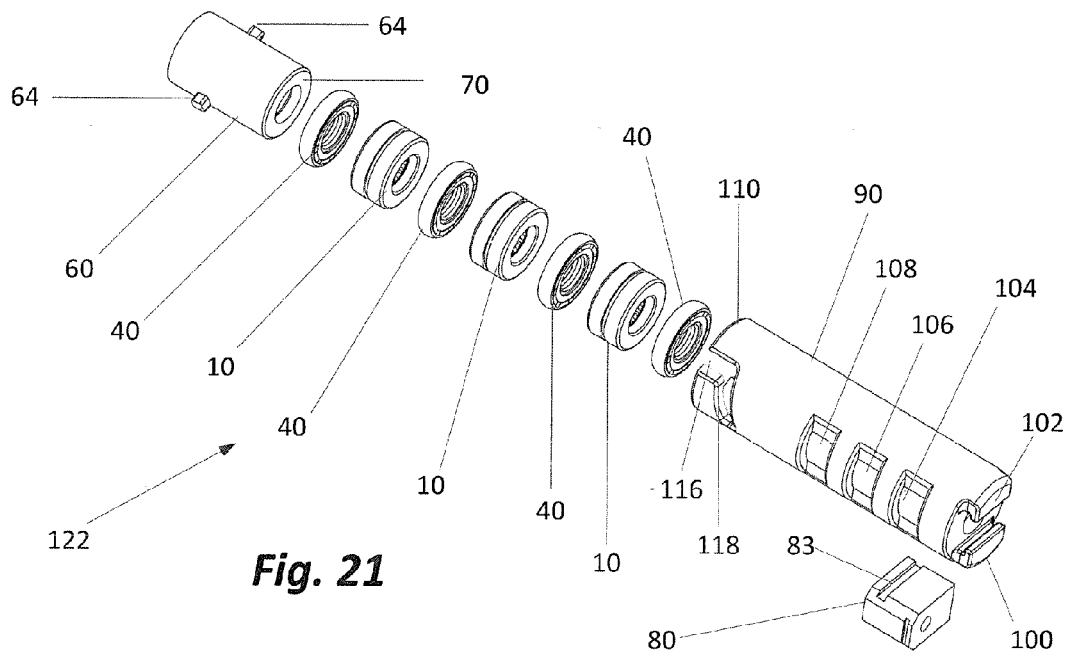
FIG. 21 is an exploded view of a subassembly.

FIGS. 21 and 22 illustrate how a subassembly 122 can be created using a sleeve 90, three spring contact rings 10, four ring seals 40, a set screw block 80, and a strain relief 60. The set screw block 30 is coupled to the sleeve 90 by inserting the fingers 100 and 102 of the sleeve 90 into the alignment channels 83 and 84 of the set screw block 80. Other mechanisms for coupling the set screw block 80 to the sleeve 90 may be employed without deviating from the invention. The set screw block 80 is then slid along the fingers 100 and 102 until the pin-receiving channel 86 of the set screw block 80 is aligned with the bore 94 of the sleeve 90. Friction between the fingers 100 and 102 and the alignment channels 83 and 84 is typically sufficient to temporarily retain the set screw block 80 in place as manufacturing of the subassembly continues. The set screw block 80 is permanently held in place by the overmold material which ultimately encapsulates the subassembly 122.

Next, ring seals 40 and spring contact rings 10 are inserted in alternating fashion into the bore 94 of the sleeve 90. Finally, a strain relief 60 is inserted and locked in place. Locking of the strain relief 60 to the sleeve 90 is achieved by inserting the end 70 of the strain relief into the bore 94 of the sleeve 90 through end 110, aligning the projections 64 of the strain relief 60 with the straight sections 116 of the locking channels 112 and 114 of the sleeve 90, continuing to advance the strain relief 60 into the bore 94 until the projections 64 reach the camming sections 118 of the locking channels 112 and 114 and then turning the strain relief 60 relative to the sleeve 90 so that the projections 64 enter the camming sections 118. As the sleeve and strain relief are turned relative to each other, cooperation between the projections and walls of the camming section 118 cause the strain relief to be locked in place and because of the angle of the camming sections, drawn toward the arrangement of seals and spring contact rings. As shown in FIG. 22, a ring seal 40 resides between the set screw block 80 and the adjacent spring contact ring 10. Likewise, a ring seal 40 resides between the strain relief 60 and the adjacent spring contact ring 10. Alternatively, a seal could be built into either the set screw block 80 or the strain relief 60.

Once the subassembly shown in FIGS. 21-22 is complete, various tests may be performed to ensure the quality of the subassembly. If a part is not performing to specifications at this stage, it is still possible to disassemble the subassembly, replace any defective parts or otherwise make repairs.

After such testing is completed and the results analyzed, a molding pin (not shown) can be inserted through the pin-receiving channel of the subassembly formed by alignment of the bores of the strain relief 50, seals 40, spring contact rings 10 and setscrew block 80. The molding pin will prevent the overmold material from entering the pin receiving channel during the overmolding process. Known techniques for overmolding can then be employed to complete the header.

One advantage of overmolding is that it serves to lock in position the various components of the subassembly 122. This is particularly true if the overmolding is performed by injection molding at a pressure which will compress or collapse the sleeve 90 without crushing the sleeve 90. The collapsed sleeve 90 will also cooperate with the ring seals 40 to electrically isolate the spring contact rings 10 from each other and from the strain relief 60 and the set screw block 80. As the wall of the sleeve 90 collapses, the outer walls of the sealing rings 40 deform while the inner walls of the sealing rings substantially maintain their shape.

Pressures which will suitably compress or collapse the sleeve 90 without crushing the sleeve 90 will depend on the material from which the sleeve 90 is made and the thickness of the sleeve 90. By way of example and without limitation, a sleeve 90 made of PEEK having a thickness of 0.035-0.045 inches will not compress adequately if the mold pressure is below about 16000 pounds per square inch (psi) and will crush if the mold pressure is above about 25000 psi. Therefore, if sleeve 90 is made of PEEK and has a thickness of 0.035-0.045 inches, the molding pressure should be in the range of about 16000 psi to about 25000 psi if, however, the sleeve 90 has the same thickness, but is made of 40% glass-filled PEEK, a molding pressure in excess of 25000 psi will be required to adequately compress the sleeve to adequately lock the components of the subassembly 122 in place. After the overmolding step is completed, the header 120 is removed from the mold and the molding pin is removed exposing the bore in which a lead terminal pin may be inserted to form electrical connections between the wires of the lead and the spring contact rings 10 of the header 120.

Other techniques may also be used to lock the components of the subassembly in place. For example, the header casing 124 and the subassembly 122 may be exposed to an annealing temperature which partially collapses the wall of the sleeve 90 to lock the spring contact rings 10, ring seals 40, strain relief 60 and the set screw block 80 in place, e.g., in a position in which (a) adjacent spring contact rings 10 and ring seals 40 are in contact with each other and the bores through the strain relief 60, each of the spring contact rings 10 and ring seals 40, and the set screw block 80 are aligned with each other; and (b) the wall of the sleeve 90 and ring seals 40 cooperate to electrically isolate each of the spring contact rings 10 from each other and the spring contact rings 10 from the set screw block 80 and the strain relief 60. Alternatively, only the subassembly 122 might be subjected to the annealing temperature. This could be done before overmolding or before inserting the subassembly into a bore of a preformed header casing 124. When the header casing 124 is formed by overmolding the subassembly 122, the overmold material will mechanically secure the header casing 124 to the subassembly 122. When the header casing 124 is preformed with a bore 126, some means (e.g., a suitable adhesive or mechanical structure) should be employed to lock the subassembly 122 in place within the bore 126 of the header casing 124.

Figure 23:
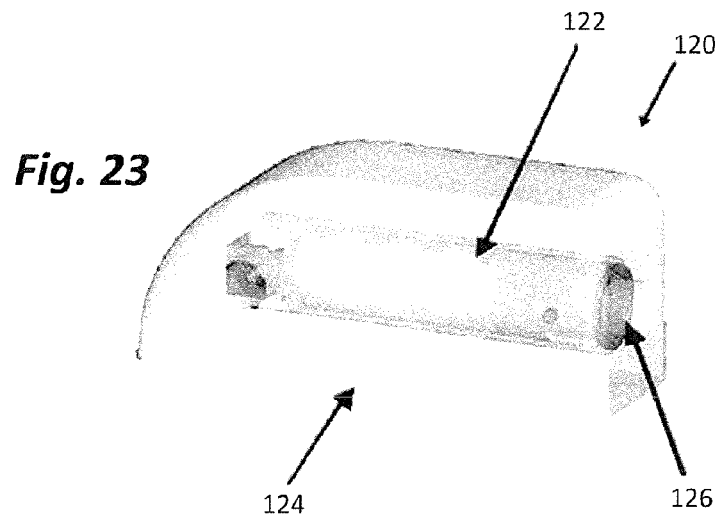
FIG. 23 is a perspective view of a header.

FIG. 23 shows a completed header 120. If the overmold material 124 is a clear material, the sleeve of the subassembly 122 will be visible as shown in FIG. 23. During overmolding, the in allows the entrance to the pin-receiving channel 126 to remain open.

Strain relief 60 can be composed of various rigid materials, encompassing: (1) either amorphous or semi-crystalline polymers within the categories defined as engineering, high performance or ultra polymers, including poly-ethyl-ethyl-ketone, polysulfone, polyurethane, polyphenylene, polyimides, liquid, crystal, polycarbonate, polyamide, ABS, COC, or alloys thereof; (2) ceramics and its alloys (3) metallic alloys of SS 316L, MP35N and titanium; however, the present invention is not limited to these materials.

Set screw block 80 can be made using more adaptable CNC machining or metal injection molding (MIM) methods, requiring less setup, fewer parts and minimal assembly, lowering associated manufacturing costs. Materials of construction used within the art of making block 80 are alloys of stainless steel 316L, titanium and MP35N.

Connector seals 40 can be made using more adaptable injection molding methods, requiring less setup, fewer parts and minimal assembly, lowering associated manufacturing costs. Materials of construction used within the art of making connector seal 40 are liquid silicone used to overmold a stiff substrate made of a non-conductive material such as PEEK. Examples of other materials suitable for use include: (1) either amorphous or semi-crystalline polymers within the categories defined as engineering, high performance or ultra polymers, including poly-ethyl-ethyl-ketone, polysulfone, polyurethane, polyphenylene, polyimides, liquid crystal, polycarbonate, polyamide, ABS, COC, or alloys thereof; (2) ceramics and its alloys; (3) metallic alloy of SS 316L, MP35N and titanium.

Thus, embodiments of the ELECTRICAL CONNECTOR SLEEVE are disclosed. One skilled in the art will appreciate the present teachings can be practiced with embodiments other than those disclosed. The disclosed embodiments are presented for purposes of illustration and not limitation, and the present teachings are limited only by the following claims.

What is claimed is:

1. A method of manufacturing a header for an implantable pulse generator comprising:
    a. forming a plurality of spring contact rings, each spring contact ring having a bore; a plurality of ring seals, each ring seal having a bore; a sleeve having a wall surrounding a bore; and a strain relief having a bore;
    b. forming a subassembly by (a) inserting the plurality of spring contact rings and the plurality of ring seals into the bore of the sleeve such that the wall of the sleeve surrounds each of the plurality of spring contact rings and each of the plurality of ring seals and each spring contact ring is separated from any adjacent spring contact ring by a ring seal, and (b) inserting at least a portion of the strain relief into the bore of the sleeve to secure the spring contact rings and ring seals in a position in which adjacent spring contact rings and ring seals are in contact with each other and the bores through the strain relief and each of the spring contact rings and rings seals of the subassembly are aligned with each other;
    c. inserting a molding pin through the bores of the strain relief and each of the spring contact rings and ring seals of the subassembly;
    d. overmolding the subassembly to lock the spring contact rings, ring seals and strain relief of the subassembly in position; and
    e. removing the molding pin; wherein the step of inserting at least a portion of the strain relief into the bore of the sleeve includes (a) aligning a projection with a channel, said channel having a straight section and a camming section angled from the straight section, (b) moving the strain relief into the bore of the sleeve until the projection reaches the camming section, and (c) twisting the strain relief relative to the sleeve to cause the projection to enter the camming section.

2. The method of claim 1 further including the step of testing the subassembly before performing the overmolding step.

3. The method of claim 1 wherein the step of overmolding is performed at a pressure which partially collapses the wall of the sleeve to thereby lock the spring contact rings, ring seals and strain relief of the subassembly in position with respect to each other and electrically isolate each of the spring contact rings of the subassembly from each other through the cooperation of the wall of the sleeve and the ring seals of the subassembly.

4. The method of claim 1 wherein the sleeve further comprises a plurality of windows, each window adjacent to one of the spring contact rings of the subassembly, and the method further includes passing at least one wire through a window and electrically coupling the at least one wire to the spring contact ring adjacent to the window.

5. The method of claim 4 wherein, during the overmolding step, some of the material used to perform the overmolding step enters a window to assist in locking at least one of the spring contact rings in position.

6. The method of claim 1 wherein the camming section is angled from the straight section at an angle other than 90 degrees.

7. The method of claim 1 wherein, during the overmolding step, some of the material used to perform the over molding step enters the channel to assist in locking at least the strain relief in position.

8. The method of claim 1 wherein the step of forming a plurality of ring seals includes forming at least one ring seal so it includes a rigid core having exposed portions which act as a stop for maintaining a predefined minimum distance between two of the adjacent spring contact rings.

9. The method of claim 8 wherein the rigid core also prevents the inner diameter of the ring seal from deforming during the overmolding step even as the outer diameter of the sealing ring deforms.

10. The method of claim 9 wherein said rigid core is made of PEEK and other portions of the ring seals are made of silicone.

11. The method of claim 1 wherein at least one of the spring contact rings includes a ring and a spring having spiral, radial cut spring fingers.

12. The method of claim 1 wherein the sleeve is formed to include structures on its outer surface for supporting at least one other component of the header.

13. The method of claim 12 wherein such other component is a tip block.

14. The method of claim 12 wherein such other component is another subassembly.

15. The method of claim 1 wherein the strain relief includes a seal for electrically isolating the strain relief from the spring contact rings of the subassembly.

16. The method of claim 1 wherein the step of overmolding is performed at a pressure which partially collapses the wall of the sleeve and deforms the outer walls of the sealing rings while the inner walls of the sealing rings substantially maintain their shapes to thereby lock the spring contact rings, ring seals and strain relief of the subassembly in position with respect to each other and electrically isolate the spring contact rings of the subassembly from each other through the cooperation of the wall of the sleeve and the ring seals of the subassembly.

17. A method of manufacturing a header for an implantable pulse generator comprising:
   a. forming a plurality of spring contact rings, each spring contact ring having a bore; a plurality of ring seals, each ring seal having a bore; a sleeve having a wall surrounding a bore; and a strain relief having a bore;
   b. forming a subassembly by (a) inserting the plurality of spring contact rings and the plurality of ring seals into the bore of the sleeve such that the wall of the sleeve surrounds each of the plurality of spring contact rings and each of the plurality of ring seals and each spring contact ring is separated from any adjacent spring contact ring by a ring seal, and (b) inserting at least a portion of the strain relief into the bore of the sleeve to secure the spring contact rings and ring seals in a position in which adjacent spring contact rings and ring seals are in contact with each other and the bores through the strain relief and each of the spring contact rings and rings seals of the subassembly are aligned with each other;
   c. inserting a molding pin through the bores of the strain relief and each of the spring contact rings and ring seals of the subassembly;
   d. overmolding the subassembly to lock the spring contact rings, ring seals and strain relief of the subassembly in position; and
   e. removing the molding pin; wherein the sleeve is formed to include structures on its outer surface for supporting an RF antenna.

* * * * *